(12) United States Patent
Dandekar et al.

(10) Patent No.: US 6,911,568 B1
(45) Date of Patent: Jun. 28, 2005

(54) REGENERATION OF AROMATIC ALKYLATION CATALYSTS USING HYDROCARBON STRIPPING

(75) Inventors: Ajit B. Dandekar, Fairfax, VA (US); John P. McWilliams, Swedesboro, NJ (US); C. Morris Smith, West University Place, TX (US); Michael A. Better, Kingwood, TX (US); Wei-Ping Tai, Yardley, PA (US)

(73) Assignee: ExxonMobil Oil Corporation, Irving, TX (US)

( * ) Notice: Subject to any disclaimer, the term of this patent is extended or adjusted under 35 U.S.C. 154(b) by 0 days.

(21) Appl. No.: 10/239,372

(22) PCT Filed: Apr. 28, 2000

(86) PCT No.: PCT/US00/11403

§ 371 (c)(1),
(2), (4) Date: May 28, 2003

(87) PCT Pub. No.: WO01/83408

PCT Pub. Date: Nov. 8, 2001

(51) Int. Cl.[7] .................................................. C07C 2/66
(52) U.S. Cl. ...................................................... 585/467
(58) Field of Search .............................. 585/467; 502/31

(56) References Cited

U.S. PATENT DOCUMENTS

| | | | | |
|---|---|---|---|---|
| 3,851,004 A | * | 11/1974 | Yang | 585/467 |
| 4,876,408 A | * | 10/1989 | Ratcliffe et al. | 585/467 |
| 5,959,168 A | * | 9/1999 | van der Aalst et al. | 585/323 |
| 6,096,935 A | * | 8/2000 | Schulz et al. | 585/323 |

* cited by examiner

*Primary Examiner*—Thuan D Dang
(74) *Attorney, Agent, or Firm*—Darryl M. Tyus; Linda A. Kubena

(57) ABSTRACT

A process for alkylating an alkylatable aromatic compound is disclosed, in which the process includes:

(a) contacting the alkylatable aromatic compound and an alkylating agent with an alkylation catalyst under alkylation conditions; and (b) when said alkylation catalyst has become at least partially deactivated, contacting said alkylation catalyst with a $C_1$–$C_8$ hydrocarbon under alkylation catalyst reactivation conditions.

The process provides comparable rejuvenation of catalyst activity as air rengenaration with minimal or no increase in amounts of undesirable byproducts such as polypropylbenzenes in the case of benzene alkylation with propylene.

14 Claims, 1 Drawing Sheet

REGENERATION OF AROMATIC ALKYLATION CATALYSTS USING HYDROCARBON STRIPPING

CROSS REFERENCING OF THE APPLICATION

This application is a Continuation-in-Part of PCT/US00/11403 filed Apr. 28, 2000.

FIELD OF THE INVENTION

This invention relates to a process for alkylating an aromatic compound using an alkylation catalyst, in which the spent alkylation catalyst is subjected to regeneration by stripping with a hydrocarbon.

BACKGROUND OF THE INVENTION

Zeolite-based catalysts, such as MCM-22, are effective catalysts for hydrocarbon conversion reactions, such as the liquid phase alkylation of benzene with olefins to yield monoalkylated products with high selectivity. As in all catalytic processes, the catalyst deactivates with time on stream and needs to be regenerated to recover activity. Typically, zeolite catalysts are regenerated ex situ by flowing air to burn off coke and remove other deactivating species. However, in addition to loss in production time for catalyst removal, shipment, off-site regeneration, and replacement, conventional air regeneration of these catalysts results in a drop in the monoalkylation selectivity.

For example, the Mobil/Raytheon process for producing cumene involves the liquid phase alkylation of benzene with propylene, followed by transalkylation of di- and tri- isopropyl benzene with benzene. MCM-22 has been used successfully as the alkylation and transalkylation catalysts in this process and is particularly attractive because of its high selectivity towards monoalkylated products. However, the regeneration of used cumene catalysts, such as MCM-22 and the like, at the end of their cycles has been shown to result in an increase in the amounts of undesirable polypropylbenzenes and other heavy byproducts formed during subsequent operations. This results in a significantly increased duty on the transalkylator and a consequent drop in overall yield and product purity. It is highly desirable therefore to adopt a regeneration protocol which minimizes this change in the selectivity to undesirable byproducts.

There is a need in the art to provide a process for regenerating zeolite-based, aromatic alkylation catalysts without the drawbacks discussed above.

According to the invention, it has now been found that stripping in a light hydrocarbon gas stream like propane at relatively mild conditions effectively rejuvenates spent aromatic alkylation catalyst without any loss in the monoalkylation selectivity. The novel procedure of the present disclosure provides an efficient and convenient way for in situ regeneration of spent aromatic alkylation catalysts, significantly enhancing their re-use value.

SUMMARY OF THE INVENTION

The present invention relates to a process for alkylating an aromatic compound comprising the steps of:
(a) contacting an alkylatable aromatic compound and an alkylating agent with an alkylation catalyst under alkylation conditions; and
(b) when said alkylation catalyst has become at least partially deactivated, contacting said alkylation catalyst with a $C_1$–$C_8$ hydrocarbon under alkylation catalyst reactivation conditions.

Preferably, the contacting step (b) is effected with a $C_1$–$C_8$ alkane.

Preferably, the contacting step (b) is effected with a $C_3$–$C_5$ alkane.

Preferably, the alkylation catalyst reactivation conditions include a temperature of at least 200° F. (93° C.).

Preferably, the alkylation catalyst is selected from MCM-22, MCM-36, MCM-49, MCM-56 and zeolite beta.

Preferably, the aromatic compound is benzene, the alkylating agent is ethylene or propylene and the contacting step (a) is effected under substantially liquid phase conditions.

DETAILED DESCRIPTION OF THE INVENTION

Figure 1:
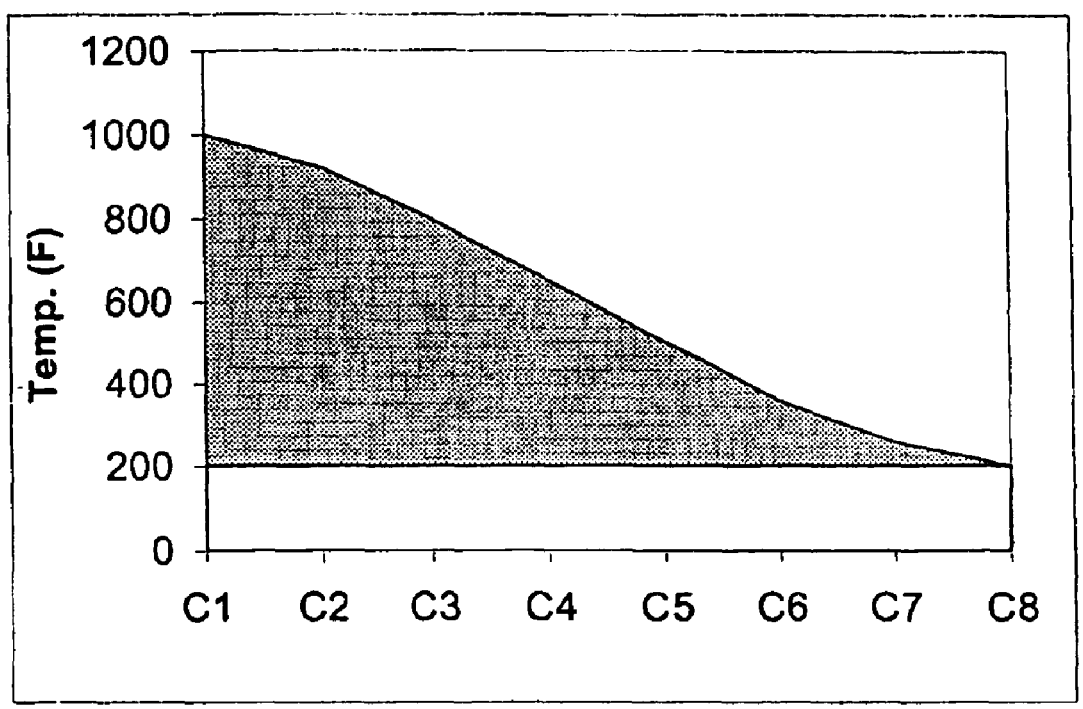
FIG. 1 shows suitable temperature conditions for stripping a spent or used zeolite catalyst with various hydrocarbons at atmospheric pressure.

The present invention relates to a process for the production of a monoalkylated aromatic compound, particularly ethylbenzene or cumene, by the liquid phase alkylation of an alkylatable aromatic compound with an alkylating agent in the presence of an alkylation catalyst. More particularly, the invention is concerned with a process in which, when the alkylation catalyst has become at least partially deactivated, the catalyst is subjected to an in-situ catalyst reactivation step, in which the deactivated alkylation catalyst is contacted with a $C_1$–$C_8$ hydrocarbon under conditions which effectively rejuvenate the catalyst without loss of its monoalkylation selectivity.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful, provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, toluene, xylene, naphthalene, anthracene, naphthacene, perylene, coronene and phenanthrene.

Generally, the alkyl groups which can be present as substituents on the aromatic compound contain from one to about 22 carbon atoms, for example from about one to eight carbon atoms, and in particular from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cyxene, butylbenzene, pseudocumene, o-diethylbenzene, m-diethylbenzene, p-diethylbenzene, isoainylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-imethylanthracene;

9-ethylanthracene; 2-methylanthracene; o-methylanthracene; 9,10 dimethylphenanthrene; and 3-methyl-phenanthrene. Higher molecular weight alkylaromatic hydrocarbons can also be used as starting materials, and these would include aromatic bydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, and pentadecyltoluene. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances is less than about 500 ppm.

Refonmate containing substantial quantities of benzene, toluene and/or xylene constitutes a particularly useful feed for the alkylation process of this invention.

The alkylating agents which are useful in the process of this invention generally include any organic compound having at least one available alkylating group capable of reaction with the alkylatable aromatic compound. Preferably, the alkylating group possesses from 1 to 5 carbon atoms. Examples of suitable alkylating agents are olefins such as ethylene, propylene, the butenes and the pentenes; alcohols (inclusive of monoalcohols, dialcohols, and trialcohols) such as methanol, ethanol, the propanols, the butanols and the pentanols; aldehydes such as formaldehyde, acetaldehyde, propionaldehyde, butyraldehyde and n-valeraldehyde; and, alkyl halides such as methyl chloride, ethyl chloride, the propyl chlorides, the butyl chlorides and the pentyl chlorides.

Mixtures of light olefins are especially useful as alkylating agents in the alkylation process of this invention. Accordingly, mixtures of ethylene, propylene, butenes and/ or pentenes which are major constituents of a variety of refinery streams, e.g., fuel gas, gas plant off-gas containing ethylene and propylene, naphtha cracker off-gas containing light olefis and refinery FCC propane/propylene streams, are useful aklylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation catalyst employed in the process of the invention is a molecular sieve which is selective to the production of monoalkylated species, such as ethylbenzene and cumene. Suitable molecular sieves include MCM-22 (described in detail in U.S. Pat. No. 4,954,325), PSH-3 (described in detail in U.S. Pat. No. 4,439,409), SSZ-25 (described in detail in U.S. Pat. No. 4,826,667), MCM-36 (described in detail in U.S. Pat. No. 5,250,277), MCM-49 (described in detail in U.S. Pat. No. 5,236,575), MCM-56 (described in detail in U.S. Pat. No. 5,362,697), and zeolite beta (described in detail in U.S. Pat. No. 3,308,069). The molecular sieve can be combined in conventional manner with an oxide binder, such as alumina, such that the final alkylation catalyst contains between 2 and 80 wt % sieve. Alternatively, the molecular sieve can be used in self-bound form that is without a separate oxide binder.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C. (32° F. to about 932° F.), and preferably between about 50° C. (122° F.) to about 250° C. (482° F.), a pressure of from about 0.2 to about 250 atmospheres, and preferably from about 5 to about 100 atmospheres, a molar ratio of alkylatable aromatic compound to alkylating agent of from about 0.1:1 to about 50:1, and preferably can be from about 0.5:1 to about 10:1, and a feed weight hourly space velocity (WHSV) of between about 0.1 and 500 $hr^{-1}$, preferably between 0.5 and 100 $hr^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction may be carried out in the liquid phase. Suitable liquid phase conditions include a temperature between 300° F. and 600° F. (about 150° C. and 316° C.), preferably between 400° F. and 500° F. (about 205° C. and 260° C.), a pressure up to about 3000 psig (20875 kPa), preferably between 400 and 800 psig (2860 and 5600 kPa), a space velocity between about 0.1 and 20 WHSV, preferably between 1 and 6 WHSV, based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may also take place under liquid phase conditions including a temperature of up to about 250° C. (482° F.), e.g., a temperature up to about 150° C. (300° F.), e.g., a temperature from about 10° C. (50° F.) to about 125° C. (257° F.); a pressure of about 250 atmospheres or less, e.g., a pressure from about 1 to about 30 atmospheres; and an aromatic hydrocarbon weight hourly space velocity (WHSV) of from about 5 $hr^{31\ 1}$ to about 250 $hr^{-1}$, preferably from 5 $hr^{-1}$ to 50 $hr^{-1}$.

As the alkylation process of the invention proceeds, the alkylation catalyst will gradually lose its alkylation activity, such that the reaction temperature required to achieve a given performance parameter, for example conversion of the alkylating agent, will increase. According to the invention, when the alkylation catalyst has become at least partially deactivated, i.e., alkylation activity of the catalyst has decreased by some predetermined amount, typically at least 10%, more preferable 40–80% and, most preferably, 40–70%, compared to the initial alkylation activity of the catalyst, the deactivated catalyst is subjected to reactivation by stripping with a $C_1$–$C_8$ hydrocarbon, preferably a $C_1$–$C_8$ alkane, more preferably with a $C_3$–$C_5$ alkane and most preferably with propane.

The reactivation conditions may vary depending on the type of, and the number of carbon atoms in, the hydrocarbon selected. In general, the reactivation is carried out at a temperature of at least 200° F. (93° C.). However, the reactivation temperature should not be so high as to result in significant cracking of the reactivating hydrocarbon. FIG. 1 illustrates suitable reactivation temperatures at atmospheric pressure for the various $C_1$–$C_8$ alkanes. Preferably, the reactivation temperature is 300° F. to 500° F. (150° C. to 260° C.).

The reactivation is conveniently carried out at a pressure between about 1 atm and 50 atm, a WHSV between about 0.01 and 50 $hr^{-1}$ for a time sufficient to increase the activity of the alkylation catalyst to 80–100% of its original activity, typically for 0.1 hours to 30 days, more preferably from 1 to 24 hours.

The hydrocarbon stripping process of the invention may be repeated a number of times during the lifetime of the alkylation catalyst and, when the stripping process fails to achieve the required increase in catalytic activity, the catalyst can be subjected to a conventional air regeneration.

The alkylation process of the invention is particularly intended to produce monoalkylated aromatic compounds, such as ethylbenzene and cumene, but the alkylation step will normally produce some polyalkylated species. Thus the process preferably includes the further steps of separating the polyalkylated species from the alkylation effluent and reacting them with additional aromatic feed in a transalkylation reactor over a suitable transalkylation catalyst. The transalkylation catalyst is preferably a molecular sieve which is selective to the production of the desired monoalkylated species and can, for example, employ the same molecular sieve as the alkylation catalyst, such as MCM-22, MCM-36, MCM-49, MCM-56 and zeolite beta. In addition, the transalkylation catalyst may be ZSM-5, zeolite X, zeolite Y, and mordenite, such as TEA-mordenite.

The transalkylation reaction of the invention is conducted in the liquid phase under suitable conditions such that the polyalkylated aromatics react with the additional aromatic feed to produce additional monoalkylated product. Suitable transalkylation conditions include a temperature of 100° C. to 260° C. (212° F. to 500° F.), a pressure of 10 to 50 bar (200–600 kPa), a weight hourly space velocity of 1 to 10 on total feed, and a benzene/polyalkylated benzene weight ratio of 1:1 to 6:1.

When the polyalkylated aromatics are polyethylbenzenes and are reacted with benzene to produce ethylbenzene, the transalkylation conditions preferably include a temperature of 220° C. to 260° C. (428° F. to 500° F.), a pressure of 20 to 30 bar, weight hourly space velocity of 2 to 6 on total feed and a benzene/PEB weight ratio of 2:1 to 6:1.

When the polyalkylated aromatics are polypropylbenzenes and are reacted with benzene to produce cumene, the transalkylation conditions preferably include a temperature of 100° C. to 200° C. (212° F. to 392° F.), a pressure of 20 to 30 bar, weight hourly space velocity of 1 to 10 on total feed and a benzene/PIPB weight ratio of 1:1 to 6:1.

As the transalkylation catalyst becomes deactivated, it may be subjected to the same hydrocarbon stripping process as described above in relation to the alkylation catalyst.

The invention will now be more particularly described with reference to the following Examples. In the Examples, catalyst performance is defined by reference to the kinetic rate constant which is determined by assuming second order reaction kinetics. For a discussion of the determination of the kinetic rate constant, reference is directed to "Heterogeneous Reactions: Analysis, Examples, and Reactor Design, Vol. 2: Fluid-Fluid-Solid Reactions" by L. K. Doraiswamy and M. M. Sharma, John Wiley & Sons, New York (1994) and to "Chemical Reaction Engineering" by O. Levenspiel, Wiley Eastern Limited, New Delhi (1972).

EXAMPLE 1

MCM-22 catalyst was prepared by extruding 65 wt % MCM-22 crystal with 35 wt % alumina into 1/16" extrudate. 1 g of the catalyst was charged to an isothermal well-mixed Parr autoclave reactor along with a mixture comprising of benzene (156 g) and propylene (28 g). The reaction was carried out at 266° F. (130° C.) and 300 psig (2170 kPa) for 4 hours. A small sample of the product was withdrawn at regular intervals and analyzed by gas chromatography. The catalyst performance was assessed by the kinetic rate constant based on propylene conversion, as well as cumene selectivity at 100% propylene conversion, and is described in Example 5.

EXAMPLE 2

Benzene alkylation with propylene was then conducted on the fresh MCM-22 catalyst used in Example 1 in a fixed-bed reactor at 262° F. (128° C.) and 275 psig (2000 kPa) at a benzene to propylene molar ratio of 3.8. The catalyst was exposed to 7.4 $hr^{-1}$ of benzene and 0.53 $hr^{-1}$ of propylene for 4 months. The corresponding spent catalyst activity parameter at the end of the cycle and the cumene selectivity are given in Example 5.

EXAMPLE 3

The spent cumene catalyst from Example 2 was subjected to flowing air at a gas hourly space velocity of 300 $hr^{-1}$ at 1000° F. (about 540° C.) for 12 hours. One gram of the final catalyst was evaluated for benzene alkylation with propylene according to the procedure described in Example 1. Catalyst performance is compared with the fresh and spent catalysts in Example 5.

EXAMPLE 4

The spent cumene catalyst from Example 2 was subjected to propane stripping at a WHSV of 0.16 $hr^{-1}$ for 8 hours at 400° F. (204° C.). One gram of the final catalyst was evaluated for benzene alkylation with propylene according to the procedure described in Example 1. Catalyst performance is compared with the fresh and spent catalysts in Example 5.

EXAMPLE 5

The performance of fresh MCM-22 catalyst from Example 1, spent MCM-22 catalyst from Example 2, air-regenerated spent MCM-22 catalyst from Example 3 and propane-stripped catalyst from Example 4 are compared in Table 1. The data represent catalyst performance based on the kinetic rate constant as well as cumene selectivity at 100% propylene conversion. A comparison of activity regained as well as the increase in polypropylbenzene (PPB) make after rejuvenation is also included.

TABLE 1

| Catalyst | Kinetic Rate Constant | Cumene Selectivity (wt %) | % Loss in Activity | % Increase in PPB Make |
|---|---|---|---|---|
| Example 1 | 84 | 82.1 | — | — |
| Example 2 | 40 | 82.9 | 52.3 | Nil |
| Example 3 | 77 | 76.5 | 8.3 | 36 |
| Example 4 | 74 | 82.5 | 11.9 | Nil |

The results in Table 1 demonstrate that the use of a hydrocarbon stream, such as propane, to clean the spent catalyst surface produces a comparable rejuvenation of catalyst activity as that produced by air-regeneration but without the 36% increase in polypropylbenzene make obtained with the air-regenerated catalyst.

What is claimed is:

1. A process for alkylating an alkylatable aromatic compound comprising the steps of:
   (a) contacting an alkylatable aromatic compound and an alcylating agent with an alkylation catalyst under alkylation conditions, wherein said alkylation catalyst is selected fom MCM-22, PSH-3, SSZ-25, MCM-36, MCM-49, MCM-56 and zeolite beta; and
   (b) when said alkylation catalyst has become at least partially deactivated, contacting said alkylation catalyst with a $C_1$–$C_8$ alkane gas under alkylation catalyst reactivation conditions.

2. The process as claimed in claim 1, wherein the contacting step (b) is effected with a $C_3$–$C_5$ alkane.

3. The process as claimed in claim 1, wherein the alcylation catalyst reactivation conditions include a temperature of at least 200° F. (93° C.).

4. The process as claimed in claim 1, wherein the alkylation catalyst reactivation conditions include a temperature between about 300° F. and 500° F. (150° C. to 260° C.), a pressure between about 1 and 50 atm, a WHSV between about 0.01 and 50 $hr^{-1}$, and a time between about 0.1 hours and 30 days.

5. The process as claimed in claim 1, wherein the alkylatale aromatic compound is benzene, the alkylating agent is ethylene or propylene and the containing step (a) is effected under substantially liquid phase conditions.

6. The process as claimed in claim 1, wherein said alkylation catalyst is MCM-22.

7. The process as claimed in claim 1, wherein said alkylation catalyst is PSH-3.

8. The process as claimed in claim 1, wherein said alkylation catalyst is SSZ-25.

9. The process as claimed in claim 1, wherein said alkylation catalyst is MCM-36.

10. The process as claimed in claim 1, wherein said alkylation catalyst is MCM-49.

11. The process as claimed in claim 1, wherein said alkylation catalyst is MCM-56.

12. The process as claimed in claim 1, wherein said alkylation catalyst is zeolite beta.

13. A process for alkylating an alkylatable aromatic compound comprising the steps of:
   (a) contacting an alkylatable aromatic compound and an alkylating agent with an alkylation catalyst under alkylation conditions, wherein said alkylation catalyst is selected from the group consisting of MCM-22, PSH-3, SSZ-25, MCM-36, MCM-49, MCM-56 and zeolite beta; and
   (b) when said alkylation catalyst has become at least partially deactivated, contacting said alkylation catalyst with a $C_1$–$C_3$ alkane gas under alkylation catalyst reactivon conditions.

14. The process as claimed in claim 13, wherein said alkane is a $C_3$ alkane.

* * * * *